United States Patent [19]

Wright

[11] 4,029,882

[45] June 14, 1977

[54] SELECTIVE ACYLATION OF THE C-1 AMINO GROUP OF AMINOGLYCOSIDE ANTIBIOTICS

[75] Inventor: John J. Wright, Orange, N.J.

[73] Assignee: Schering Corporation, Kenilworth, N.J.

[22] Filed: Mar. 19, 1974

[21] Appl. No.: 452,586

[52] U.S. Cl. .............................. 536/17; 424/180; 424/181; 536/10
[51] Int. Cl.$^2$ .................................... C07H 15/22
[58] Field of Search ............... 260/210 AB, 210 K; 536/17

[56] References Cited

UNITED STATES PATENTS

| | | | |
|---|---|---|---|
| 3,244,590 | 4/1966 | Schaffner et al. | 260/210 AB |
| 3,753,973 | 8/1973 | Umezawa et al. | 260/210 AB |
| 3,780,018 | 12/1973 | Konishi et al. | 260/210 AB |
| 3,781,268 | 12/1973 | Kawaguchi et al. | 260/210 AB |
| 3,792,037 | 2/1974 | Kawaguchi et al. | 260/210 AB |
| 3,796,698 | 3/1974 | Naito et al. | 260/210 AB |
| 3,796,699 | 3/1974 | Naito et al. | 260/210 AB |
| 3,828,021 | 8/1974 | Beattie et al. | 260/210 AB |
| 3,868,360 | 2/1975 | Daniels et al. | 260/210 AB |

OTHER PUBLICATIONS

Julian et al., "Chem. Abst." vol. 75, 1971, p. 316592.

*Primary Examiner*—Johnnie R. Brown
*Attorney, Agent, or Firm*—Carver Joyner; Stephen Coan; Raymond McDonald

[57] ABSTRACT

A novel process for preparing novel 1-N-acyl-4,6-di-(aminoglycosyl)aminocyclitols is disclosed. The compounds are useful as antibacterial agents.

18 Claims, No Drawings

SELECTIVE ACYLATION OF THE C-1 AMINO GROUP OF AMINOGLYCOSIDE ANTIBIOTICS

This invention relates to semisynthetic antibacterial agents. More particularly, this invention relates to semisynthetic aminoglycoside aminocyclitol antibacaterial agents prepared from antibiotics elaborated principally but not exclusively by species of microorganisms from Micromonospora and *Streptomycetes genera*. In particular, this invention relates to semisynthetic aminoglycoside aminocyclitol antibacterial agents wherein the C-1 amino group of the aminocyclitol moiety bears an acyl group and to the non-toxic acid addition salts of such agents. This invention also relates to methods for acylating aminoglycoside aminocyclitol antibiotics at the C-1 amino position to produce acyl derivatives wherein the acyl function optionally bears an amino and/or a hydroxy substituent.

Prior Art

U.S. Pat. No. 3,541,078, issued Nov. 15, 1970, describes an antibiotic complex which is elaborated by strains of *Bacillus circulans*. The complex consists of two members designated ambutyrosin A and ambutyrosin B (butyrosin A and B). The antibiotics are of the aminoglycoside-aminocyclitol class but are unique in that the aminocyclitol moiety, 2-deoxystreptamine, is acylated at the C-1 amino position by a hydroxyaminoacyl group, the group being derived from $\alpha$-hydroxy-$\gamma$-aminobutyric acid (HABA).

In a publication by Akita et al. in the Journal of Antibiotics (Japan) 23, 173–183 (1970) is set forth the chemical structure of an antibiotic designated SF-755 which antibiotic was subsequently named, ribostamycin. Ribostamycin is structurally related to butyrosin B but does not have a HABA group on the 2-deoxystreptamine moiety. However, Kawaguchi et al. [The Journal of Antibiotics (Japan) 25, No. 12, 741-2]successfully acylated ribostamycin at the C-1 amino position of the 2-deoxystreptamine moiety with L-(-)-$\alpha$-hydroxy-$\gamma$-aminobutyric acid and obtained an improved antibiotic having activity against some ribostamycin resistant organisms. By applying an acylation technique to kanamycin A, Kawaguchi and his coworkers produced an antibiotic having substantially enhanced applied use characteristics when compared with kanamycin. The antibiotic has been designated BB-K8, [see the Journal of Antibiotics (Japan), 25, No. 12, 695-731].

More recently, U.S. Pat. No. 3,780,018, issued December 18, 1973, describes a process whereby 1-[L-(-)-$\gamma$-amino-$\alpha$-hydroxybutyryl]gentamicin $C_1$ are 2'-[L-(-)-$\gamma$-amino-$\alpha$-hydroxybutyryl]gentamicin $C_1$ are prepared by reacting gentamicin $C_1$ with a blocked active ester of L-(-)-$\gamma$-amino-$\alpha$-hydroxybutyric acid (HABA) followed by deblocking via methods known to the art and separation of the reaction mixture by chromatographic means. All of the above-noted prior art processes are effected by reacting the antibiotic free nitrogen base with a blocking group or by acylating the unblocked free nitrogen base with an acylating agent.

I have discovered a process for preparing novel 1-N-acyl derivatives of 4,6-di-(aminoglycosyl)aminocyclitol antibiotics which comprises reacting a partially neutralized acid addition salt of such antibiotic with an acylating agent which agent may optionally bear a hydroxy and/or an amino substituent and separating the acylated antibiotic from the reaction medium.

SUMMARY OF THE INVENTION

In one of its process aspects, this invention may be set forth as follows: A process for 1-N-acylating 4,6-di-(amino-glycosyl) aminocyclitol antibiotics which comprises reacting a partially neutralized acid addition salt of such antibiotic with an acylating agent derived from a carboxylic acid having 1 to 8 carbon atoms, said acylating agent being unsubstituted or mono substituted by a substituent selected from the group consisting of hydroxy and amino.

In another of its process aspects, this invention may be set forth as follows: In the process for preparing 1-N-hydroxyaminoacyl derivatives of 4,6-di-(aminoglycosyl)aminocyclitol antibiotics by acylating such antibiotics with an acylating agent derived from a carboxylic acid having 3 to 8 carbon atoms, said acylating agent bearing a hydroxy and an amino substituent on different carbon atoms, the improvement which comprises acylating a partially neutralized acid addition salt of said antibiotic.

In its product aspect, this invention may be described as a 1-N-Z-4,6-di-(aminoglycosyl)aminocyclitol antibacterial agent selected from the group consisting of 1-N-Z-gentamicin A, 1-N-Z-gentamicin B, 1-N-Z-gentamicin $B_1$, 1-N-Z-gentamicin $C_1$, 1-N-Z-gentamicin $C_{1a}$, 1-N-Z-gentamicin $C_2$, 1-N-Z-gentamicin $C_{2a}$, 1-N-Z-gentamicin $X_2$, 1-N-Z3', 4'-dideoxykanamycin B, 1-N-Z-sisomicin, 1-N-Z-verdamicin, 1-N-Z-tobramycin, 1-N-Z-antibiotic G-418, 1-N-Z-antibiotic 66-40B, 1-N-Z-antibiotic 66-40D, 1-N-Z-antibiotic JI-20A, 1-N-Z-antibiotic JI-20B, 1-N-Z-antibiotic G-52, 1-N-Z-mutamicin 1, 1-N-Z-mutamicin 2, 1-N-Z-mutamicin 4, 1-N-Z-mutamicin 5, 1-N-Z-mutamicin 6, and the non-toxic acid addition salts thereof wherein Z is an acyl group derived from a hydrocarbon carboxylic acid having 1 to 5 carbon atoms, said acyl group being unsubstituted or mono substituted by either hydroxy or amino, said acyl group being straight chain, branched chain or cyclic, said acyl group also being saturated or unsaturated with the proviso that when Z is formyl or is unsaturated it must also be unsubstituted. Exemplary of the acyl groups embraced by the product aspect of this invention are formyl, acetyl, propionyl, propenoyl, butyryl, isobutyryl, cyclopropylcarbonyl, hydroxyacetyl, aminoacetyl, 4-hydroxybutyryl, 4-aminobutyryl and the like.

Blocking groups and methods for employing the same are well known in the art. For example, such groups and methods are described in the patents and publications referred to hereinabove under, "Prior Art." In those instances wherein the desired acyl derivative bears a hydroxy substituent, such substituent may be protected (blocked) by acylating the same.

As used herein, the terms "blocking group" or "protecting group" refers to groups which render the blocked or protected amino and/or hydroxy groups inert to subsequent desired chemical manipulation, but which can easily be removed at the end of the synthetic sequence without cleaving the desired N-aminoacyl or N-aminohydroxyacyl or N-hydroxyacyl group.

As used herein, the term "partially neutralized acid addition salt" means that each mole or antibiotic has less than a stoichiometric number of moles of acid associated therewith, i.e., less than the "per" acid addition salt. For example, one equivalent or gentamicin $C_1$ having five amino groups would require five equivalents of acid to form the "per" acid addition salt. The process of this invention is effected on an acid addition salt of gentamicin $C_1$ having less than five equivalents of acid; four for example. Further, the term "acid addition salt" embraces such salts as may be formed between the basic antibiotic and an acid without regard to whether the acid may be termed inorganic or organic. Exemplary of acids embraced by the term are sulfuric, hydrochloric, phosphoric, nitric, acetic, propionic, succinic, oxalic, cyclopropylcarboxylic, trimethylacetic, maleic, benzoic, phenylacetic, trifluoroacetic or the like.

Aminoglycoside antibiotics and amines in general are usually more readily manipulated as acid addition salts than as free nitrogen bases. Thus, the process of this invention provides such advantage, whereas the prior art processes using the free nitrogen bases do not. Further, the partially neutralized acid addition salts used herein are produced in situ thereby permitting the use of the "per" acid addition salt as starting material. Acylating agents are generally known in the art, however, in the process of acylating a 4,6-di-(aminoglycosyl)aminocyclitolantibiotic certain acylating agents are preferred. Thus, in those instances wherein the acyl group Z is unsubstituted, the preferred acylating agent is the anhydride of the requisite acid. When Z is a hydroxyaminoacyl group, the preferred acylating agent is the N-hydroxysuccinimidyl ester of the requisite acid.

The term 4,6-di-(aminoglycosyl)aminocyclitol antibiotics embraces those aminoglycoside antibiotics wherein the aminoglycoside moieties are joined to the aminocyclitol moiety by glycosidic linkages at positions 4 and 6. Thus, the term embraces such antibiotics as the gentamicins, kanamycin, tobramycin, sisomicin, antibiotic G-418, verdamicin and also includes others set forth herein.

The underivatized (parent) antibiotics named herein are all known in the art except the following: gentamicin $C_{2a}$, antibiotic 66-40B, antibiotic 66-40D, and the mutamicins (i.e. mutamicins 1, 2, 4, 5 and 6). Gentamicin $C_{2a}$ is disclosed and claimed in U.S. Patent Application Ser. No. 269,914, filed July 7, 1972, and now abandoned, entitled, "Novel Antibiotics From Micromonospora." The compound is a component of the antibiotic complex described in U.S. Pat. No. 3,091,572, which issued May 28, 1963. Gentamicin $C_{2a}$ may be obtained by converting the sulfate salt obtained by the procedure of Example 4 of U.S. Pat. No. 3,091,572 to the free base and by subjecting the free base to the following procedure:

Gentamicin $C_{2a}$

Dissolve 96 gms. of gentamicin base in 400 ml. of the upper phase which results when methanol, chloroform and 17% ammonium hydroxide are mixed in the volume ratio of 1:2:1. Add one tenth of the solution to each of the first ten tubes in a 500x 80 ml. tube counter current extractor. Fill all of the tubes including the first ten to capacity with the lower phase of the above-described solvent mixture. Set the solvent reservoir to deliver 40 ml. of upper phase to tube one (1) for each transfer. Set the apparatus for 500 transfers. When the transfers are complete, sample every eighth tube for chromatography (in duplicate) on Schleicher and Schuell paper No. 589 using the lower phase of the above-described solvent mixture. Permit the chromatograms to develop for about 16 hours then dry the papers. Plate one paper on an agar plate seeded with *Staphylococcus aureus* (A.T.C.C. 6538P), spray the duplicate with the conventional ninhydrin solution and heat to develop. Incubate the agar plate at 37° C overnight and combine the solution from tubes containing the material that migrates like gentamicin $C_1$ (i.e., tubes 290–360).

Replace tubes 290–360 with fresh tubes containing 40 ml. of upper phase and 40 ml. lower phase. Re-set the apparatus for an additional 2800 transfers and repeat the chromatographic procedure performed above. Combine tubes 1–16 and concentrate in vacuo to obtain 1.3 gms. of Antibiotic $C_{2a}$.

Antibiotics 66-40B and 66-40D are disclosed and claimed in U.S. Application Ser. No. 335,185, filed Feb. 23, 1972, and now abandoned, entitled, "Novel Antibacterial Agents from *Micromonospora inyoensis*." The mutamicins are described and claimed in U.S. Application Ser. No. 443,052, filed Feb. 15, 1974, new U.S. Pat. No. 3,880,829, entitled Mutamicins and Process for the Preparation Thereof."

Formula I is set forth below, in order to further describe what is meant by 4,6-di-(aminoglycosyl)aminocyclitol antibiotics. In Formula I the antibiotic is shown in the nonplanar form.

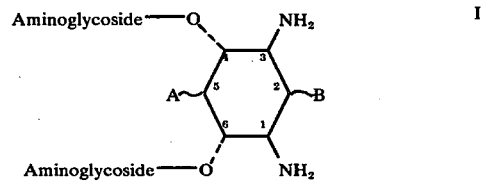

wherein A and B denote the plurality of substituents which an aminocyclitol may bear and wherein the wavy lines denote that the substituents may be in any of the possible stereochemical forms.

Thus, it may be seen that the aminoglycoside moieties on the left are glycosidically linked to positions 4 and 6, of the aminocyclitol.

The compounds of this invention are antibacterial agents having a broader spectrum of activity than their underivatized counterpart. This broader spectrum is usually manifest in the ability of the compounds of this invention to inhibit bacterial strains that are resistant to the underivatized (parent) antibiotic. Thus, the compounds disclosed and claimed herein have the potential of becoming commercially important antibacterial agents. The compounds of this invention may be employed for the same uses as their underivatized (parent) antibiotics, e.g. they may be used as a bacteriotatic rinse for hospital glassware, surgical instruments, bath tubs or the like.

In addition to their utility as antibacterial agents, the compounds of this invention are useful as intermediates in the preparation of a novel class of compounds which also possess unexpectedly enhanced antibacterial activity. Evidence of this utility may be found in the application of Wright, J. J.; Daniels, P. J. L.; Mallams, A. K. and Nagabhushan, T. L. entitled, "1-N-Alkyl-4,6-di-(aminoglycosyl)-1,3-diaminocyclitols, Methods for Their Manufacture, Methods for Their Use as Antibacterial Agents, and Compositions Useful Therefor." The application bears the Ser. No. 452,600 and is being filed concomitantly herewith, now abandoned.

EXAMPLE 1

1-N-Acetylsisomicin

Dissolve 1.25 g of sisomicin sulfate in 200 ml. of methanol — water (2:3, v/v) and chill the solution. Add 1.5ml of acetic anhydride and after approximately 10 minutes add 0.125 ml. of triethylamine in 10 ml of methanol over a 15 minute interval. Allow the reaction mixture to warm to room temperature over a 2 hour interval then evaporate the solvent in vacuo. Dissolve the residue in water and convert the product to the free base by passage of an aqueous solution thereof through Amberlite IRA-401resin in the hydroxide ion cycle. Lyophilize the column eluate the chromatograph the residue on 50 g of silica gel using the lower phase of (2:1:1) chloroform, methanol, 7% ammonium hydroxide solvent system as eluant. Monitor the fractions via TLC and combine like fractions to obtain thereby the title compound.

Yield —0.185 g, M.P. 128°–130°, $[\alpha]_D^{26°} = 159°$ (0.3% $H_2O$), nmr: ($D_2O$)ω 1.22(3H, s, —C—$CH_3$); 2.02 (3H, s, NH,—CO—$CH_3$); 2.53 (3H, s, N—$CH_3$) 4.88 (1H, M, = CH—); 5.08 (1H, d, J = 4Hz, $H_1''$); 5.35 (1H, d, J = Hz, $H_1'$). Mass spectrum: (M + 1)$^+$m/e 490, M+ m/e 489.

In a similar manner, treat an equivalent quantity of the sulfate salt of the following antibiotics to the process of Example 1:

gentamicin $C_1$, gentamicin X,
gentamicin $C_{1a}$, gentamicin A,
gentamicin $C_2$, 3′,4′-dideoxykanamycin B,
gentamicin $C_{2a}$, verdamicin
tobramycin, gentamicin B, and
antibiotic G-418, gentamicin $B_1$.
antibiotic 66-40B,
antibiotic 66-40D,
antibiotic JI-20A,
antibiotic JI-20B,
antibiotic G-52
mutamicin 1,
mutamicin 2,
mutamicin 4,
mutamicin 5,
mutamicin 6, Isolate the respective products in the manner described in Example 1 and obtain thereby the following:

1-N-acetylgentamicin $C_1$,
1-N-acetylgentamicin $C_{1a}$.
1-N-acetylgentamicin $C_2$,
1-N-acetylgentamicin $C_{2a}$,
1-N-acetylgentamicin X,
1-N-acetylgentamicin A,
1-N-acetyl-3′,4′-dideoxykanamycin B,
1-N-acetyl verdamicin
1-N-acetyl tobramycin,
1-N-acetyl antibiotic G-418,
1-N-acetyl antibiotic 6640B,
1-N-acetyl antibiotic 6640D,
1-N-acetyl antibiotic JI-20A,
1-N-acetyl antibiotic JI-20B,
1-N-acetyl antibiotic G-52,
1-N-acetylmutamicin 1,1-N-acetylgentamicin B, and
1-N-acetylmutamicin2,1-N-acetylgentamicin $B_1$. 1-N-acetylmutamicin 4,
1-N-acetylmutamicin 5,
1-N-acetylmutamicin 6,

EXAMPLE 2

1-N-Propionylsisomicin

Dissolve 1.25 g of sisomicin sulfate in 200 ml of methanol -water (2:3, v/v) and chill the solution. Add 1.5 ml of propionic ahydride followed by 0.125 ml of triethylamine in 10 ml of methanol over a 15 minute interval. Allow the reaction mixture to warm to room temperature over a 2 hour interval then evaporate the solvent in vacuo. Dissolve the residue in water and convert the product to the free base by passage of an aqueous solution thereof through Amberlite IRA-401S resin in the hydroxide ion cycle. Lyophilize the column eluate and chromatograph the residue on 50 g of silica gel using the lower phase of (2:1:1) chloroform, methanol, 7% ammonium hydroxide solvent system as eluant. Monitor the fraction via TLC and combine like fractions to obtain thereby 1-N-propionylsisomicin.

Yield 0.18 g M.P. 125°–130° C, $[\alpha]_D^{26°} + 147°$ (0.3% $H_2O$) nmr: ($D_2O$) δ1.08 (3H, t, J = 7.5Hz, $CH_2$-$CH_3$); 1:18 (3H, s, C-$CH_3$); 2.25 (2H, m, $CH_2CH_3$); 2.48(3H, s,NH$CH_3$); 4.87 (1H, m, = CH-); 5.07 (1H, d, J = 4Hz, $H_1''$); 5.34(1H, d, H = 2Hz, $H_1'$). Mass spectrum (M = 1)$^+$m/e 504, (M)$^+$m/e = 503.

In a similar manner, treat an equivalent quantity of acid addition salt of the following antibiotics to the process of Example 2:

gentamicin $C_1$, gentamicin $C_{2a}$.
gentamicin $C_{1a}$, gentamicin X, gentamicin $C_2$, gentamicin A,
3′, 4′-dideoxykanamycin B, gentamicin B, and
verdamicin, gentamicin $B_1$.
tobramycin,
antibiotic G-418
antibiotic 66-40B,
antibiotic 66-40D,
antibiotic JI-20A,
antibiotic JI-20B,
antibiotic G-52,
mutamicin 1,
mutamicin 2,
mutamicin 4,
mutamicin 5,
mutamicin 6, Isolate the respective products in the manner described in Example 2 and obtain thereby the following:

1-N-propionylgentamicin $C_1$.
1-N-propionylgentamicin $C_{1a}$.
1-N-propionylgentamicin $C_2$,
1-N-propionylgentamicin $C_{2a}$,
1-N-propionylgentamicin X,
1-N-propionylgentamicin A,
1-N-propionyl-3′, 4′-dideoxykanamycin B,
1-propionylverdamicin,
1-N-propionyltobramycin,
1-N-propionylantibiotic G-418,
1-propionylantibiotic 66-40B,
1-N-propionylantibiotic 66-40D,
1-N-propionylantibiotic JI-20A,
1-N-propionylantibiotic JI-20B, 1-N-propionylantibiotic G-52,
1-N-propionylmutamicin 1,
1-N-propionylmutamicin 2,
1-N-propionylmutamicin 4,
1-N-propionylmutamicin 5
1-N-propionylmutamicin 6,
1-N-propionylgentamicin B, and
1-propionylgentamicin $B_1$.

EXAMPLE 3

1-N-Acetylverdamicin

Dissolve 1.25 g of verdamicin sulfate in a mixture of 10 ml of methanol and 25 ml of water. Add 0.125 ml of triethylamine followed by 1.5 ml of acetic anhydride. Chill the solution to 0°–5° C and allow to react for a 15 minute interval. Allow the reaction mixture to warm to room temperature over a 2 hour interval then evaporate the solvent in vacuo. Dissolve the residue in water and convert the product to the free base by passage of an aqueous solution thereof through a suitable anion exchange resin column in the hydroxide ion cycle e.g. Amberlite IRA-401S. Lyophilize the column eluate the chromatograph the residue on 50 g of silica gel using the lower phase of (2:1:1) chloroform, methanol, 7% ammonium hydroxide solvent system as eluant. Monitor the fractions via TLC and combine like fractions to obtain 1-N-acetylverdamicin.

Yield — 0.241 g

By the process of Example 3, other 1-N-acyl derivatives of verdamicin may be prepared, such as those wherein the acyl group is derived from propionic, butyric, isobutyric or valeric acids or the like. In like manner, 1-N-acyl derivatives of other 4,6-di-(aminoglycosyl)aminocyclitol antibiotics, such as those set forth after Example 2, may be prepared.

EXAMPLE 4

1-N-Acetylgentamicin $C_1$

Dissolve 250 mg of gentamicin $C_1$ sulfate in a mixture of 25 ml of water and 10 ml of methanol. Add 0γml of triethylamine. Allow the solution to stand for ten minutes then add 0.5 ml of acetic anhydride. Let the solution stand for one hour at room temperature then evaporate to a residue in vacuo. Dissolve the residue in water and treat with Amberlite IRA 401S in the hydroxyl ion form. Filter the suspension and lyophilize the filtrate. Chromatograph the residue over a silica gel column containing 30 g of adsorbent using the lower phase of a chloroform, methanol, 7% ammonium hydroxide (2:1:1) system and obtain thereby the product of this example.

Yeild — 50 mg $[\alpha]D^{26} = +124°$ Mass Spectrum $(M + 1)^+$ m/e = 520 nmr $(D_2O)$ δ1.01 (3H, d, J = 6.5 Hz, -CHCH$_3$); 1.15 (3H, s, C-CH$_3$); 1.95 (3H, s, COCH$_3$); 2.28)3H, s, 6' NCH$_3$); 2.45 (3H, s, 3''NCH$_3$); 5.03 (1H, d, J = 4.5 Hz, $H_1$ ''); 5.09 (1H, d, J = 3.5 Hz, $H_1$ ').

EXAMPLE 5

1-N-(S-4-Amino-2-Hydroxybutyryl)Gentamicin $C_{1a}$.

A. 1-N-(S-4-Benzyloxycarbonylamino-2-Hydroxybutyryl)Gentamicin $C_{1a}$

Dissolve 2.8 g (4 m moles) of gentamicin $C_{1a}$ sulfate in 30 ml of water and add 15 ml. of methanol. Add 0.56 ml (4 m moles) of triethylamine and stir for 10 minutes. Add a solution containing 4 m moles of N-(S-4-benzyloxycarbonylamino-2-hydroxybutyryloxy)succinimide in 20 ml of dry dimethylformamide dropwise with stirring to the antibiotic solution. Stir the mixture overnight (16 hrs.) at ambient temperature. Thin layer chromatography of the reaction mixture via TLC on silica gel using the lower phase of a solvent system consisting of chloroform, methanol and ammonium hydroxide, (1:1:1), shows the presence of a plurality of minor components and one major component. Concentrate the reaction mixture to a residue in vacuo and triturate the residue with methanol to yield 3.2 g of white solids containing all the components previously observed by chromatography.

Chromatograph 150 mg of the product on 50 g of silica gel using the lower phase of a solvent system consisting of chloroform, methanol, and ammonium hydroxide, (2:1:1). Pool the fractions containing the major component and lyophilize to give 1-N-(S-4-benzyloxy-carboyxlamino-2-hydroxybutyryl)gentamicin $C_{1a}$.

Yield = 70 mg. nmr $(D_2O)$ δ1.15 (3H, s, CH$_3$); 2.49 (3H, s, NCH$_3$); 4.10 (1H, dd, J=8.0, 4.0 Hz, sidechain H-20; 7.36 (5H, m, phenyl).

B. 1-N-(S-4-Amino-2-Hydroxybutyryl)Gentamicin $C_{1a}$

Dissolve the product of step A in a mixture consisting of 12 ml of methanol and 3 ml of water, add 20 mg of 10% palladium on carbon and hydrogenate at 59 psi at room temperature. After 3 hours the reaction is essentially complete. Remove the catalyst by filtration and lyophilize the filtrate and obtain 46 mg of 1-N-(S-4-amino-2-hydroxybutyryl)gentamicin $C_{1a}$. nmr $(D_2O)$ δ1.17 (3H, s, C-CH$_3$); 2.48 (3H, s, NCH$_3$); 4.22 (1H, dd, J=9.5 Hz, 4.0 Hz, side chain CHOH); 5.04 (2H, m, H-1', and H-1''). Mass Spectral data: $(M-H_2O)$ m/e 532.

EXAMPLE 6

1-N-(S-4-Amino-2-Hydroxybutyryl)Gentamicin B

A. 1-N-(S-4-Benzyloxycarbonylamino-2-hydroxybutyryl) gentamicin B

Dissolve 3.39 g of gentamicin B sulfate in 48.4 ml of water and dilute with 23.7 ml of methanol. Add 0.7 of triethylamine dropwise with stirring. Dissolve 1.67 g of N-(S-4-benzyloxycarbonylamino-2-hydroxybutyryloxy)succinimide in dimethylformamide and add the solution dropwise with stirring to the antibiotic solution. Stir the resulting solution at room temperature for 18 hours then concentrate to a residue in vacuo. Dissolve the residue in water and treat with dilute barium hydroxide solution with stirring until the pH reaches about 8.0. Remove the precipitated barium sulfate by filtration using a filter aid. Wash the precipitate with water, combine the filtrate and washings and concentrate to a dryness in vacuo. Chromatrograph the residue on a column containing 600 g of silica gel using the lower phase of a solvent system consisting of chloroform, methanol, ammonium hydroxide (1:1:1) as the eluant. Pool the material which is eluted immediately ahead of gentamicin B and concentrate the pooled fractions to dryness and obtain thereby 1-N-(S-4-benzyloxycarbonylamino-2-hydroxybutyryl) gentamicin B as an amorphous solid.

Yield =0.2 g nmr $(D_2O)$ : δ1.27 (3H, s, C-CH$_3$); 2.51 (3H, s, NCH$_3$); 5.08 (1H, d, J=4 Hz); 5.25 (1H, d, J=3.5 Hz). B. 1-N-(S-4-amino-2-hydroxybutyryl) gentamicin B Dissolve the product of step A in a mixture consisting of 20 ml of water and 8 ml of methanol. Hydrogenate the product in the presence of 60 mg of 5% palladium-on-carbon at 50 psi and room temperature for 3 hours. Remove the catalyst by filtration through a filter aid. Wash the filter pad with water and combine the filtrate and washings. Concentrate the combined filtrate and washings to dryness in vacuo. Chromatograph the residue on a silica gel column containing 10 g of silica gel using a solution consisting of chloroform, methanol, ammonium hydroxide (2:1:1) as the eluant. Fractions containing the most polar component are pooled, concentrated and lyophilized to give 1-N-(S-4-amino-2-hydroxybutyryl) gentamicin B.

Yield = 12 mg

In a similar manner, treat an equivalent quantity of the following 4,6-di-(aminoglycosyl) aminocyclitol antibiotics to the process of Example 6:

gentamicin $C_1$,
gentamicin $C_2$,
gentamicin $C_{2a}$,
gentamicin A,
gentamicin X,
3', 4'-dideoxykanamycin B,
tobramycin,
antibiotic G-418,
antibiotic JI-20A,
antibiotic JI-20B, and
gentamicin $B_1$.

Isolate the respective products in the manner described in Example 6 and obtain thereby the following:

1-N-(S-4-amino-2-hydroxybutyryl)gentamicin $C_1$,
1-N-(S-4-amino-2-hydroxybutyryl)gentamicin $C_2$,
1-N-(S-4-amino-2-hydroxybutyryl)gentamicin $C_{2a}$,
1-N-(S-4-amino-2-hydroxybutyryl)gentamicin A,
1-N-(S-4-amino-2-hydroxybutyryl)gentamicin X,
1-N-(S-4-aminio-2-hydroxybutyryl)-3', 4'-dideoxykanamycin B,
1-N-(S-4-amino-2-hydroxybutyryl)tobramycin,
1-N-(S-4-amino-2-hydroxybutyryl)antibiotic G-418,
1-N-(S-4-amino-2-hydroxybutyryl)antibiotic JI-20A,
1-N-(S-4-amino-2-hydroxybutyryl)antibiotic JI-20B, and
1-N-(S-4-amino-2-hydroxybutyryl)gentamicin $B_1$.

In an analogous manner, by substituting an equivalent quantity of N-(S-3-benzyloxycarbonylamino-2-hydroxypropionyl) skuccinimide for N-(S-4-benzyloxycarbonylamino-2-hydroxybutyryl) succinimide, and by treating the above-named antibiotics to the process of Example 6, the following products may be obtained:

1-N-(S-3-amino-2-hydroxypropionyl)gentamicin $C_1$,
1-N-(S-3-amino-2hydroxypropionyl)gentamicin $C_2$,
1-N-(S-3-amino-2-hydroxypropionyl)gentamicin $C_{2a}$,
1-N-(S-3-aminio-2-hydroxypropionyl)gentamicin A,
1-N-(S-3-amino-2-hydroxypropionyl)gentamicin X,
1-N-(S-3-amino-2-hydroxypropionyl)-3', 4'-dideoxykanamycin B,
1-N-(S-3-amino-2-hydroxypropionyl)tobramycin,
1-N-(S-3-amino-2-hydroxypropionyl)antibiotic G-418,
1-N-(S-3-amino-2-hydroxypropionyl)antibiotic JI-20A,
1-N-(S-3-amino-2-hydroxypropionyl)antibiotic JI-20B, and
1-N-(S-3-amino-2-hydroxypropionyl)gentamicin $B_1$.

EXAMPLE 7

1-N-(S-4-Amino-2-hydroxybutyryl)verdamicin

A. 1-N-(S-4-Phthalimido-2-hydroxybutyryl)verdamicin

Dissolve 5.00 g of verdamicin sulphate in 50 ml of water and add 25 ml of methanol. Add 0.50 ml of triethylamine and stir for 10 minutes. Add a solution containing 2.5 g of N-(S-4-phthalimido-2-hydroxybutyryloxy)succinimide in 10 ml of dimethylformamide dropwise with stirring. Stir the mixture overnight at ambient temperature then concentrate to a residue in vacuo. Chromatograph the residue over 160 g of silica gel, eluting with the lower phase of a chloroform:methanol:concentrated ammonium hydroxide (1:1:1) solvent mixture. Combine and evaporate fractions containing the major component of the reaction (determined by TLC on silica gel plates) and obtain thereby the compound of this example as a white amorphous solid.

B. 1-N-(S-4-Amino-2-hydroxybutyryl)verdamicin

Dissolve the product of step A in 40 ml of ethanol and add 0.2 g of hydrazine hydrate. Reflux the solution for 2 hours, then evaporate to dryness in vacuo. Chromatograph the residue over 160 g of silica gel, eluting with the lower phase of a chloroform:methanol:concentrated ammonium hydroxide (1:1:1) solvent mixture. Combine and evaporate fractions containing the major component of the reaction (determined by TLC on silica gel plates) and obtain thereby the compound of this example as a white amorphous solid.

In a similar manner, subject to the process described in Example 7 an equivalent quantity of the following antibiotics:

sisomicin,
antibiotic G-52,
antibiotic 66-40B,
antibiotic 66-40D,
mutamicin 1,
mutamicin 2,
mutamicin 4,
mutamicin 5, and
mutamicin 6.

Isolate the respective products in the manner described in Example 7 and obtain thereby the following:

1-N-(S-4-amino-2-hydroxybutyryl)sisomicin,
1-N-(S-4-amino-2-hydroxybutyryl)antibiotic G-52,
1-N-(S-4-amino-2-hydroxybutyryl)antibiotic 66-40B,
1-N-(S-4-amino-2-hydroxybutyryl)antibiotic 66-40D,
1-N-(S-4-amino-2-hydroxybutyryl)mutamicin 1,
1-N-(S-4-amino-2-hydroxybutyryl)mutamicin 2,
1-N-(S-4-amino-2-hydroxybutyryl)mutamicin 4,
1-N-(S-4-amino-2-hydroxybutyryl)mutamicin 5, and
1-N-(S-4-amino-2-hydroxybutyryl)mutamicin 6.

In an analogous manner, by substituting an equivalent quantity of N-(S-3-phthalimido-2-hydroxypropionyloxy) succinimide for N-(S-4-phthalimido-2-hydroxybutyryloxy)succinimide, and by treating the above-named antibiotics to the process of Example 7, the following products may be obtained:

1-N-(S-3-amino-2-hydroxypropionyl)sisomicin,
1-N-(S-3-amino-2-hydroxypropionyl)antibiotic G-52,
1-N-(S-3-amino-2-hydroxypropionyl)antibiotic 66-40B, 1-N-(S-3-amino-2-hydroxypropionyl)antibiotic 66-40D,
1-N-(S-3-amino-2-hydroxypropionyl)mutamicin 1,
1-N-(S-3-amino-2-hydroxypropionyl)mutamicin 2,
1-N-(S-3-amino-2-hydroxypropionyl)mutamicin 4,
1-N-(S-3-amino-2-hydroxypropionyl)mutamicin 5, and
1-N-(S-3-amino-2-hydroxypropionyl)mutamicin 6.

EXAMPLE 8

1-N-(5Aminopentanoyl)gentmicin $C_1$

A. 1-N-(5-Phthalimidopentanoyl)gentamicin $C_1$

Dissolve 2.5 g of gentamicin $C_1$ sulphate in 250 ml of water and add 100 ml of methanol Add 0.65 ml of triethylamine and stir for 10 minutes. Add a solution of 1.2 g N-(5 -phthalimido pentanoyloxy)succinimide in 20 ml of dry dimethylformamide dropwise with stirring to the solution of the antibiotic. Stir the mixture at ambient temperature for 16 hours. Concentrate the reaction mixture to a residue in vacuo and triturate the residue with methanol to yield 3.4 g of white solids. Chromatograph the residue on 200 g of silica gel in the lower phase of a chloroform, methanol, 7% ammonium hydroxide (2:1:1) system to give 1-N-(5-phthalimidopentanoyl) gentamicin $C_1$.

B. 1-N-(5-Aminopentamoyl)gentamicin $C_1$

Heat 0.4 g of 1-N-(5-phthalimidopentanoyl)gentamicin $C_1$ in 5 ml of 5% ethanolic hydrazine hydrate under reflux for 4 hrs. Concentrate the solution and add tetrahydrofuran to precipitate 1-N-(5-aminopentanoyl)gentamicin $C_1$ which is collected by filtration.

In a similar manner, treat an equivalent quantity of acid addition salt of the following antibiotics to the process of Example 8.

gentamicin $C_{1a}$,
gentamicin $C_2$,
gentamicin $C_{2a}$,
gentamicin X,
gentamicin A,
3',4'-dideoxykanamycin B,
verdamicin, = gentamicin B,
tobramycin, = gentamicin $B_1$, and
antibiotic G-418, = sisomicin.
antibiotic 66-40B,
antibiotic 66-40D,
antibiotic JI-20A,
antibiotic JI-20B,
antibiotic G-52,
mutamicin 1,
mutamicin 2,
mutamicin 4,
mutamicin 5,
mutamicin 6.

Isolate the respective products in the manner described in Example 8 and obtain thereby the following:

1-N-(5-aminopentanoyl)gentamicin $C_{1a}$,
1-N-(5-aminopentanoyl)gentamicin $C_2$,
1-N-(5-aminopentanoyl)gentamicin $C_{2a}$,
1-N-(5-aminopentanoyl)gentamicin X,
1-N-(5-aminopentanoyl)gentamicin A,
1-N-(5-aminopentanoyl)3',4'-dideoxykanamycin B,
1-N-(5-aminopentanoyl)verdamicin,
1-N-(5-aminopentanoyl)tobramycin,
1-N-(5-aminopentanoyl)antibiotic G-418,
1-N-(5-aminopentanoyl)antibiotic 66-40B,
1-N-(5-aminopentanoyl)antibiotic 66-40D,
1-N-(5 aminopentanoyl)antibiotic JI-20A,
1-N-(5-aminopentanoyl)antibiotic JI-20B,
1-N-(5aminopentanoyl)antibiotic G-52,
1-N-(5-aminopentanoyl)mutamicin 1,
1-N-(5-aminopentanoyl)mutamicin 2,
1-N-(5-aminopentanoyl)mutamicin 4,
1-N-(5-aminopentanoyl)mutamicin 5,
1-N-(5-aminopentanoyl)mutamicin 6,
1-N-(5-aminopentanoyl)gentamicin B,
1-N-(5-aminopentanoyl)gentamicin $B_1$, and
1-N-(5-aminopentanoyl)sisomicin.

EXAMPLE 9

1-N-(5-Hydroxypentanoyl)gentamicin $C_1$

Dissolve 2.5 g of gentamicin $C_1$ in 250 ml of water and add 100 ml of methanol. Add 0.65 ml of triethylamine and stir for fifteen minutes. Add a solution of 1.0 g of N-(5-acetoxypentanoyloxy)succinimide with stirring to the solution of the antibiotic, and stir at ambient temperature for 16 hrs. Evaporate the solution in vacuo to leave a solid residue. Dissolve the residue in 5 ml of 5% ethanolic hydrazine hydrate and heat under reflux for fifteen minutes. Concentrate the solution in vacuo to leave an oily residue and chromatograph it on 200 g silica gel in the lower phase of a solvent system consisting of chloroform, methanol and 7% ammonium hydroxide (2:1:1) to give 1-N-(5-hydroxypentanoyl)gentamicin $C_1$.

In a similar manner, treat an equivalent quantity of acid addition salt of the following antibiotics to the process of Example 9:

gentamicin $C_{1a}$, = sisomicin.
gentamicin $C_2$,
gentamicin $C_{2a}$,
gentamicin X,
gentamicin A,
3',4'-dideoxykanamycin B,
verdamicin,
tobramycin,
antibiotic G-418,
antibiotic 66-40B,
antibiotic 66-40D,
antibiotic JI-20A,
antibiotic JI-20B,
antibiotic G-52,
mutamicin 1,
mutamicin 2,
mutamicin 4,
mutamicin 5,
mutamicin 6,
gentamicin B,
gentamicin $B_1$, and Isolate the respective products in the manner described in Example 9 and obtain thereby the following:

1-N-(5-hydroxypentanoyl)gentamicin $C_{1a}$,
1-N-(5-hydroxypentanoyl)gentamicin $C_2$,
1-N-(5-hydroxypentanoyl)gentamicin $C_{2a}$,
1-N-(5-hydroxypentanoyl)gentamicin X,
1-N-(5-hydroxypentanoyl)gentamicin A,
1-N-(5-hydroxypentanoyl-3',4'-dideoxykanamycin B,
1-N-(5-hydroxypentanoyl)verdamicin,
1-N-(5-hydroxypentanoyl)tobramycin,
1-N-(5-hydroxypentanoyl)antibiotic G-418,
1-N-(5-hydroxypentanoyl)antibiotic 66-40B, 1-N-(5-hydropenanoyl)antibiotic 66-40D,
1-N-(5-hydroxypentanoyl)antibiotic JI-20A,
1-N-(5-hydroxypentanoyl)antibiotic JI-20 B,
1-N-(5-hydroxypentanoyl)antibiotic G-52,
1-N-(5-hydroxypentanoyl) mutamicin 1,
1-N-(5 -hydroxypentanoyl)mutamicin 2,
1-N-(5-hydroxypentanoyl)mutamicin 4,
1-N-(5hydroxypentanoyl)mutamicin 5,
1-N-(5-hydroxypentanoyl(mutamicin 6,
1-N-(5-hydroxypentanoyl)gentamicin B,
1-N-(5-hydroxypentanoyl)gentamicin $B_1$, and
1-N-(5-hydroxypentanoyl)sisomicin.

EXAMPLE 10

1-N-Formylgentamicin $C_1$

Dissolve 2.5 g of gentamicin $C_1$ sulphate in 250 ml of water and add 100 ml of methanol. Add 0.65 ml of triethylamine and stir for ten minutes. Add a solution of 2.0 g of N-formyloxysuccinimide in 20 ml of dry dimethylformamide dropwise with stirring to the solution of the antibiotic. Stir the mixture at ambient temperature for 16 hours. Concentrate the reaction mixture to a residue in vacuo and triturate the residue with methanol to yield the product of this example as a white amorphous solid which may optionally be further purified by the chromatographic procedure set forth in the preceding Example.

In a similar manner, treat an equivalent quantity or acid addition salt of the following antibiotics to the process of Example 10 gentamicin $C_{1a}$, sisomicin.
gentamicin $C_2$,
gentamicin $C_{2a}$,
gentamicin X,
gentamicin A,
3', 4' -dideoxykanamycin B,
verdamicin,
tobramycin,
antibiotic G-418,
antibiotic 66-40B,
antibiotic 66-40D,
antibiotic JI-20A,
antibiotic JI-20B,
antibiotic G-52,
mutamicin 1,
mutamicin 2,
mutamicin 4,
mutamicin 5,
mutamicin 6,
gentamicin B,
gentamicin $B_1$, and Isolate the respective products in the manner described in Example 10 and obtain thereby the following:

1-N-formylgentamicin $C_{1a}$,
1-N-formylgentamicin $C_2$,
1-N-formylgentamicin $C_{2a}$,
1-N-formylgentamicin X,
1-N-formylgentamicin A,
1-N-formyl-3' ,4' -dideoxykanamycin B,
1-N-formylverdamicin,
1-N-formyltobramycin,
1-N-formylantibiotic G-418,
1-N-formylantibiotic 66-40B,
1-N-formylantibiotic 66-40D,
1-N-formylantibiotic JI-20A,
1-N-formylantibiotic JI-20B,
1-N-formylantibiotic G-52,
1-N-formylmutamicin 1,
1-N-formylmutamicin 2,
1-N-formylmutamicin 4,
1-N-formylmutamicin 5,
1-N-formylmutamicin 6,
1-N-formylgentamicin B,
1-N-formylgentamicin $B_1$, and
1-N-formylsisomicin.

Although the compounds of this invention have been exemplified as the free nitrogen bases, this invention also embraces the non-toxic acid addition salts thereof such as those formed with hydrochloric, sulfuric, phophoric, propionic, maleic, tartaric, benzoic, phenylacetic, cyclopropane carboxylic acids or the like. These salts may be prepared as follows:

General Preparation of Acid Addition Salts

Dissolve the free nitrogen base of the 1-N-acyl-4,6-di (aminoglycosyl) aminocyclitol in 10 volumes of water with stirring. Using a dilute solution (e.g. 2N) of the requisite acid, adjust the solution of the antibacterial agent to ph-4.0 and lyophilize the resultant solution.

The compounds of this invention are antibacterial agents having a broader spectrum of activity than their underivatized counterpart. This broader spectrum is usually manifest in the ability of the compounds of this invention to inhibit bacterial strains that are resistant to the underivatized (parent) antibiotic. Thus, the compounds disclosed and claimed herein have the potential of becoming commercially important antibacterial agents. The compounds of this invention may be employed for the same uses as their underivatized (parent antibiotics, e.g. they may be used as a bacteriotatic rinse for hospital glassware, surgical instruments, bath tubs or the like.

In addition to their utility as antibacterial agents, the compounds of this invention are useful as intermediates in the preparation of a novel class of compounds which also possess unexpectedly enhanced antibacterial acitvity. Evidence of this utility may be found in the application of Wright, J. J., Daniels, P. J. L. Mallams, A. K. an Nagabhusham, T. L. entitled, "1-N-Alkyl-4,6-di (aminoglycosyl)-1,3-diaminocyclitols, Methods for Their Manufacture, Methods for Their Use As Antibacterial Agents, and compositions Useful Therefor." The application bears the Ser. No. 452,600 and is being filed comcomitantly herewith, now abandoned.

The following table (Table 1) sets forth the Minimal Inhibitory Concentration (MIC) of representative compounds of this invention. The tests were performed in Mueller-Hinton Broth (pH 7.2) using standard procedures.

1. 1-N-acetylgentamicin $C_1$
2. 1-N-propionylsisomicin
3. 1-N-acetylsisomicin

Table 1

| | Minimal Inhibitory Concentration Mg/kg (Mueller-Hinton Broth pH 7.2) | | |
|---|---|---|---|
| | 1 | 2 | 3 |
| E. Coli W 677/R55 * | 0.3 | 7.5 | 0.3 |
| JR 66 * | 3.0 | 7.5 | 3.0 |

Table 1-continued

| Minimal Inhibitory Concentration Mg/kg (Mueller-Hinton Broth pH 7.2) | | | |
|---|---|---|---|
| | 1 | 2 | 3 |
| St. M. 589 | 7.5 | 17.5 | 3.0 |
| Baker 2 | 3.0 | 7.5 | 3.0 |
| F-14-BK | 3.0 | 7.5 | 3.0 |
| LA 290/R55 * | 3.0 | 3.0 | 3.0 |
| ATCC 10536 | 3.0 | 3.0 | 0.75 |
| *Pseudomonas Aeruginosa* | | | |
| St. M. 762 | 17.5 | >25 | 3.0 |
| 1395 | >25 | >25 | 7.5 |
| NRRL 3223 | 7.5 | 17.5 | 3.0 |
| Stone 20 | 3.0 | 3.0 | .075 |
| Stone 39 | 17.5 | 17.5 | 3.0 |
| Stone 130 * | >25 | >25 | 3.0 |
| Stone 138 * | >25 | >25 | 3.0 |
| *Klebsiella pneumoniae* | | | |
| Adler 17 | 3.0 | 3.0 | 0.75 |
| Adler 18 | 3.0 | 3.0 | 0.75 |
| Georgetown 3694 * | 17.5 | 17.5 | 0.3 |
| Georgetown 3020 * | 3.0 | 7.5 | 0.30 |
| *Staphylococcus aureus* | | | |
| 209P | 3.0 | 17.5 | 0.75 |
| Wood | 3.0 | 7.5 | 0.3 |
| *Streptococcus pyogenes* | | | |
| C | >25 | >25 | 3.0 |
| A. Alvarez | 3.0 | 7.5 | 7.5 |
| *Bacillus subtilis* | | | |
| 6623 | .075 | 0.3 | 0.03 |

* gentamicin resistant

I claim:

1. A process for 1-N-acylating 4,6-di-(aminoglycosyl-)aminocyclitol antibiotics which comprises reacting a partially neutralized acid addition salt of such antibiotic with an acylating agent derived from a carboxylic acid having 1 to 8 carbon atoms, said acylating agent being unsubstituted, mono substituted by a substituent selected from the group consisting of hydroxy and amino, or di-substituted by one of each such substituents with the proviso that when the acylating agent is di-substituted the substituents must occupy positions on different carbon atoms.

2. A process of claim 1 wherein the acylating agent is unsubsituted.

3. The process of claim 1 wherein the acylating agent bears a hydroxy substituent.

4. The process of claim 1 wherein the acylating agent bears both an amino and a hydroxy substituent.

5. A process of claim 1 wherein the acylating agent bears an amino substituent.

6. In the process for preparing 1-N-hydroxyaminoacyl derivatives of 4,6-di-(aminoglycosyl)aminocyclitol antibiotics by acylating such antibiotics with an acylating agent derived from a carboxylic acid having 3 to 8 carbon atoms, said acylating agent bearing a hydroxy and an amino substituent on different carbon atoms, the improvement which comprises acylating a partially neutralized acid addition salt of said antibiotic.

7. A 1-N-Z-4,6-di-(aminoglycosyl)aminocyclitol antibacterial agent selected from the group consisting of 1-N-Z-gentamicin A, 1-N-Z-gentamicin B, 1-N-Z-gentamicin $B_1$, 1-N-Z-gentamicin $C_1$, 1-N-Z-gentamicin $C_{1a}$, 1-N-Z-gentamicin $C_2$, 1-N-Z-gentamicin $C_{2a}$, 1-N-Z-gentamicin X, 1-N-Z-3′,4′-dideoxykanamycin B, 1-N-Z-sisomicin, 1-N-Z-verdamicin, 1-N-Z-tobramycin, 1-N-Z-antibiotic G-418, 1-N-Zantibiotic 66-40B, 1-N-Z-antibiotic JI-20A, 1-N-Z-antibiotic JI-20B, 1-N-Z-antibiotic G-52, 1-N-Z-mutamicin 1, 1-N-Z-mutamicin 2, 1-N-Z-mutamicin 4, 1-N-Z-mutamicin 5, 1-N-Z-mutamicin 6, and the non-toxic acid addition salts thereof wherein Z is an acyl group derived from a hydrocarbon carboxylic acid having 1 to 5 carbon atoms, said acyl group being unsubstituted or mono substituted by either hydroxy or amino, said acyl group being straight chain, branched chain or cyclic, said acyl group also being saturated or unsaturated with the proviso that when Z is formyl or is unsaturated it must also be unsubstituted.

8. A compound of claim 7 wherein Z is an unsubstituted acyl group.

9. A compound of claim 7 wherein Z is mono substituted by a hydroxy group.

10. A compound of claim 7 wherein Z is mono substituted by an amino group.

11. A compound of claim 8 selected from the group consisting of 1-N-Z-gentamicin A, 1-N-Z-gentamicin B, 1-N-Z-gentamicin $B_1$, 1-N-Z-gentamicin $C_1$, 1-N-Z-gentamicin $C_{1a}$, 1-N-Z-gentamicin $C_2$, 1-N-Z-gentamicin $C_{2a}$, 1-N-Z-gentamicin X, 1-N-Z-3′, 4′-dideoxykanamycin B, 1-N-Z-sisomicin, 1-N-Z-verdamicin, 1-N-Z-tobramycin, 1-N-Z-antibiotic G-418, 1-N-Z-antibiotic 66-40B, 1-N-Z-antibiotic 66-40D, 1-N-Z-antibiotic JI-20A, 1-N-Z-antibiotic JI-20B, 1-N-Z-antibiotic G-52, 1-N-Z-mutamicin 1, 1-N-Z-mutamicin 2, 1-N-Z-mutamicin 4, 1-N-Z-mutamicin 5, 1-N-Z-mutamicin 6, and the non-toxic acid addition salts thereof wherein Z is an acyl group having 2 carbon atoms.

12. A compound of claim 8 selected from the group consisting of 1-N-Z-gentamicin A, 1-N-Z-gentamicin B, 1-N-Z-gentamicin $B_1$, 1-N-Z-gentamicin $C_1$, 1-N-Z-gentamicin $C_{1a}$, 1-N-Z-gentamicin $C_2$, 1N-Z-gentamicin $C_{2a}$, 1-N-Z-gentamicin X, 1-N-Z-3′,4′-dideoxykanamycin B, 1-N-Z-sisomicin, 1-N-Z-verdamicin, 1-N-Z-tobramycin, 1N-Z-antibiotic G-418, 1-N-Z-antibiotic 66-40B, 1-N-Z-antibiotic 66-40D, 1-N-Z-antibiotic JI-20A, 1-N-Z-antibiotic JI-20B, 1-N-Z-antibiotic G-52, 1-N-Z-mutamicin 1, 1-N-Z-mutamicin 2, 1-N-Z-mutamicin 4, 1-N-Z-mutamicin 5, 1-N-Z-mutamicin 6, and the nontoxic acid addition salts thereof wherein Z is an acyl group having 3 carbon atoms.

13. A compound of claim 8 selected from the group consisting of 1-N-Z-gentamicin A, 1-N-Z-gentamicin B, 1-N-Z-gentamicin $B_1$, 1-N-Z-gentamicin $C_1$, 1-N-Z-gentamicin $C_{1a}$, 1-N-Z-gentamicin $C_2$, 1-N-Z-gentamicin $C_{2a}$, 1-N-Z-gentamicin X, 1-N-Z-3′, 4′-dideoxykanamycin B, 1-N-Z-sisomicin, 1-N-Z-verdamicin, 1-N-Z-tobramycin, 1-N-Z-antibiotic G-418, 1-N-Z-antibiotic 66-40B, 1-N-Z-antibiotic 66-40D, 1-N-Z-antibiotic JI-20A, 1N-Z-antibiotic JI-20B, 1-N-Z-antibiotic G-52, 1-N-Z-mutamicin 1, 1-N-Z-mutamicin 2, 1-N-Z-mutamicin 4, 1-N-Z-mutamicin 5, 1-N-Z-mutamicin 6, and the nontoxic acid addition salts thereof wherein Z is an acyl group having 4 carbon atoms.

14. A compound of claim 8 selected from the group consisting of 1-N-Z-gentamicin A, 1-N-Z-gentamicin B, 1-N-Z-gentamicin $B_1$, 1-N-Z-gentamicin $C_1$, 1-N-Z-gentamicin $C_{1a}$, 1-N-Z-gentamicin $C_2$, 1-N-Z-gentamicin $C_{2a}$, 1-N-Z-gentamicin X, 1-N-Z-3′,4′-dideoxykanamycin B, 1-N-Z-sisomicin, 1-N-Z-verdamicin, 1-N-Z-tobramycin, 1-N-Z-antibiotic G-418, 1-N-Z-antibiotic 66-40B, 1-N-Z-antibiotic 66-40D, 1-N-Z-antibiotic JI-20A, 1-N-Z-antibiotic JI-20B, 1-N-Z-antibiotic G-52, 1-N-Z-mutamicin 1, 1-N-Z-mutamicin 2, 1-N-Z-mutamicin 4, 1-N-Z-mutamicin 5, 1-N-Z-mutamicin 6, and the nontoxic acid addition salts thereof wherein Z is an acyl group having 5 carbon atoms.

15. 1-N-acetyl sisomicin.
16. 1-N-acetyl verdamicin.
17. 1-N-acetyl antibiotic G-52.
18. 1-N-acetyl gentamicin $C_{1a}$.

UNITED STATES PATENT OFFICE
CERTIFICATE OF CORRECTION

Patent No. 4,029,882      Dated June 14, 1977

Inventor(s) John J. Wright

It is certified that error appears in the above-identified patent and that said Letters Patent are hereby corrected as shown below:

Column 5, line 28, "(1H, d, J = Hz, $H_1$;)" should read --(1H, d, J = 2 Hz, $H_1'$)--. Column 7, line 55, "2.28) 3H, s, 6', $NCH_3$);" should read --2.28 (3H, s, 6', $NCH_3$);--. Column 8, line 20, "(3H, s, $CH_3$);" should read --(3H, s, $C-CH_3$);--. Column 15, Claim 7, line 60 - Add --1-N-Z-Antibiotic 66-40D-- after 66-40B.

Signed and Sealed this

Twenty-first Day of February 1978

[SEAL]

Attest:

RUTH C. MASON
*Attesting Officer*

LUTRELLE F. PARKER
*Acting Commissioner of Patents and Trademarks*